(12) United States Patent
Håkansson (10) Patent No.: US 9,578,425 B2
(45) Date of Patent: Feb. 21, 2017

(54) ELECTRIC SWITCHING DEVICE (71) Applicant: Osseofon AB, Göteborg (SE)

(72) Inventor: Bo Håkansson, Göteborg (SE)

(73) Assignee: Osseofon AB, Gothenburg (SE)

( * ) Notice: Subject to any disclaimer, the term of this patent is extended or adjusted under 35 U.S.C. 154(b) by 92 days.

(21) Appl. No.: 14/451,744

(22) Filed: Aug. 5, 2014

(65) Prior Publication Data

US 2015/0045607 A1 Feb. 12, 2015

(30) Foreign Application Priority Data

Aug. 7, 2013 (SE) .................... 1300529-3

(51) Int. Cl.
*A61N 1/00* (2006.01)
*H04R 25/00* (2006.01)
*A61N 1/36* (2006.01)

(52) U.S. Cl.
CPC .......... *H04R 25/43* (2013.01); *A61N 1/36032* (2013.01); *H04R 25/606* (2013.01); *H04R 2225/67* (2013.01)

(58) Field of Classification Search
CPC .................. A61N 1/36032; A61N 2/02; H04R 25/604–25/608; H04R 2225/67; H04R 2460/13
See application file for complete search history.

(56) References Cited

U.S. PATENT DOCUMENTS

| | | | |
|---|---|---|---|
| 4,063,048 A | 12/1977 | Kissiah | |
| 5,624,376 A | 4/1997 | Ball | |
| 7,797,029 B2 | 9/2010 | Gibson | |
| 2005/0033383 A1* | 2/2005 | Ibrahim | A61N 1/36032 607/57 |
| 2005/0105752 A1 | 5/2005 | Husung | |
| 2009/0287038 A1* | 11/2009 | Parker | H04R 25/554 600/25 |
| 2011/0103627 A1 | 5/2011 | Meier et al. | |
| 2011/0112607 A1 | 5/2011 | Zierhofer | |
| 2013/0018218 A1 | 1/2013 | Haller et al. | |
| 2013/0182874 A1* | 7/2013 | Buehlmann | H04R 25/55 381/312 |

OTHER PUBLICATIONS

Woodford, Chris. "How Reed Switches Work (magnetically Operated Switches)." Explain That Stuff. N.p., n.d. Web.*
EESR in corresponding European Patent Application No. 14179854.6 dated Apr. 13, 2015.
Håkansson B., Sabine Reinfeldt, Måns Eeg-Olofsson, Per Östli, Hamidreza Taghavi, Johannes Adler, John Gabrielsson, Stefan Stenfelt, Gösta Granström, 2009, A novel bone conduction implant (BCI)—engineering aspects and preclinical studies, International journal of audiology 2010;49(3):203-15.

* cited by examiner

*Primary Examiner* — Samuel Gilbert
(74) *Attorney, Agent, or Firm* — Renner, Otto, Boisselle & Sklar, LLP.

(57) ABSTRACT

An electric switching device for an implantable hearing aid is disclosed. The device automatically, directly or indirectly activates the power consumption for an implantable hearing aid when an outer sound processor is installed on the patient and turns off/reduces the power consumption when the sound processor is removed.

7 Claims, 5 Drawing Sheets

ELECTRIC SWITCHING DEVICE

TECHNICAL FIELD

The present disclosure relates to an electric switching device which automatically, directly or indirectly, activates a power supply for an implantable hearing aid when an outer sound processor is attached to the patient and turns off/reduces the power consumption when a sound processor is removed.

BACKGROUND

Implantable hearing aids are used in many applications to rehabilitate hearing impairments of different kinds where conventional air conduction hearing aids will give a less successful treatment result, or are not feasible. One type of implantable hearing aid is the bone conduction hearing aid where a vibrator that directly stimulates the skull bone is fully implanted beneath the skin. This kind of hearing aid is prescribed to patients who are suffering from one or two sided chronic ear infections or a congenital/acquired malformation of the outer and/or middle ear or single-sided deafness. This type of implantable bone conduction hearing aid is often called Bone Conduction Implant (BCI) see Håkansson et al. 2010 and FIG. 1.

Figure 1:
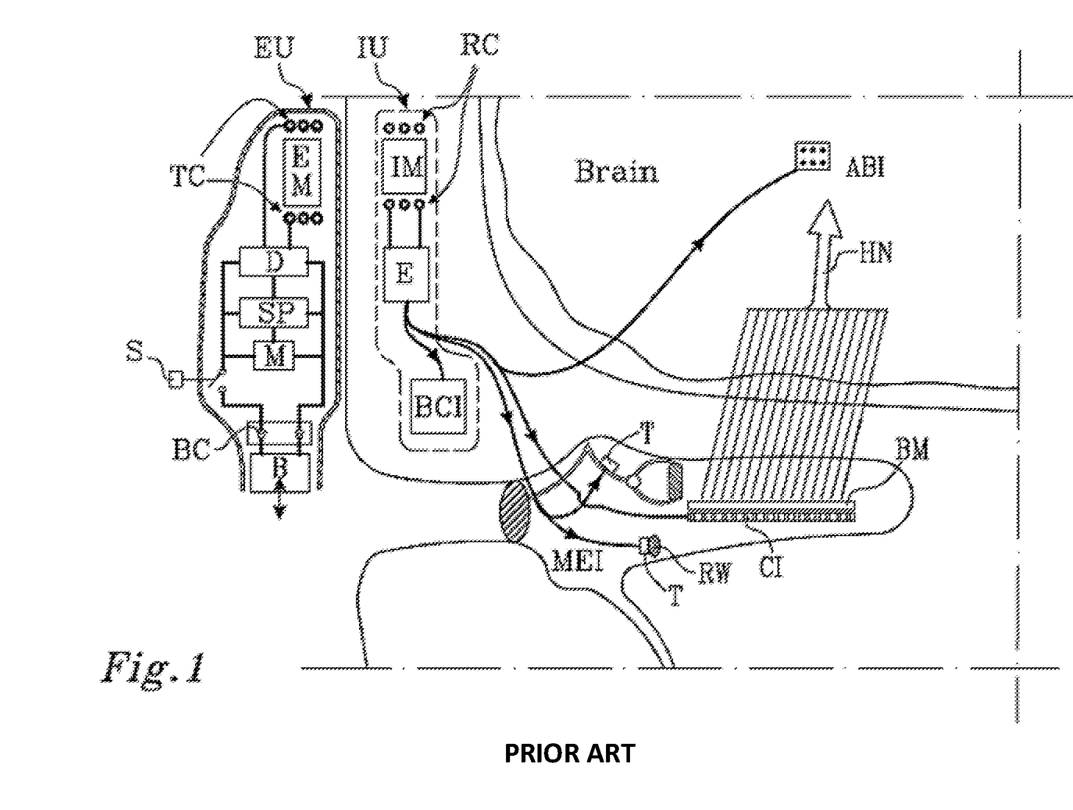
FIG. 1: Prior Art—the cross-section of an implantable hearing aid wherein the power consumption is activated by an external change-over switch (S) or that the battery (B) is removed sufficiently from the battery contact (BC). Several different applications are also shown comprising implantable bone conduction implants (BCI) with a vibrator in direct contact with the skull bone, cochlear implant (CI) with electrodes in the inner ear, brainstem implant (ABI) with electrodes in the brainstem and middle ear implant (MEI) with vibrator/loudspeaker in the middle ear.

Another type of implantable hearing aid which is also illustrated in FIG. 1 is a Cochlear Implant (CI). Cochlear Implants are used for patients suffering from considerably reduced neurogenic function with a substantial reduction of hair cells in the inner ear. The Cochlear implant stimulates the basal cells of the basilar membrane (BM) electrically inside the inner ear by means of an array of electrodes which are introduced inside the cavity of the inner ear along the basilar membrane where these cells are located (see e.g. U.S. Pat. No. 4,063,048). A similar kind of implantable hearing aid is a so called Auditory Brainstem Implant (ABI) which is also illustrated in FIG. 1. Auditory Brainstem Implants are used when the auditory nerve (HN) which conducts sound information from the inner ear to the brain is damaged and then the electrodes are applied to the brainstem (see e.g. U.S. Pat. No. 7,797,029).

Finally, there is a type of implantable hearing aid which has a mechanical loudspeaker (T) connected to one of the ossicles of the middle ear or to the round window (RW) membrane which is also illustrated in FIG. 1. This kind of hearing aid is often called Middle Ear Implant (MEI) and is prescribed to patients for whom the ordinary air conduction hearing aid is insufficient (see e.g. U.S. Pat. No. 5,624,376).

Also belonging to the group of MEI are other implants which directly or indirectly stimulate the fluids of the inner ear mechanically e.g. DACS (Direct Acoustical Cochlear Stimulator from Cochlear Corp. Australia) and MET (Middle Ear Transducer from former Otologics, USA) provided they are operated via an inductive link through intact skin (DACS and MET are not shown In FIG. 1).

These types of implantable hearing aids all have in common that they have an external unit (EU) which is sometimes denoted "sound processor" or "audio processor" as well as an implanted unit (IU), and the sound energy is transmitted from the external unit to the implanted unit via an inductive link which allows the skin and soft tissues covering over the implant to remain intact. The inductive link consists of a circular transmitter coil (TC) located in the external unit and a similar circular receiver coil (RC) which is located in the implanted unit. In order for the external unit in implantable hearing aids to remain firmly fixed in the correct location when they are used by the patient two retention magnets are typically used. Typically one external retention magnet (EM) is seated in the centre of the transmitting coil (TC) in the external unit and one implanted retention magnet (IM) is seated in the centre of the receiving coil (RC) in the implanted unit such that the coils are thereby axially centred with respect to each other. In some cases several magnets may be used on each side of the skin respectively, and in some topologies they may have different axes of magnetic polarity, but the principle function is to provide retention of the external unit to the implanted unit and to centre the coils above each other to provide the best possible inductive transmission of sound energy. FIG. 1 also illustrates that the signal, which is received by the receiving coil, is processed in an electronic unit (E) before the signal is finally driving the actuating units, respectively. In the BCI, the electronic unit (E) may advantageously be integrated in the actuating unit, together with the vibration transducer unit, encapsulated in a titanium casing.

The external unit contains, besides the transmitter coil and retention magnet, also active components such as microphone (M), signal processor (SP), driving circuits for the inductive link (D) as well as a battery (B) for the power supply. As shown in FIG. 1, the battery may easily be dismantled/replaced (see double headed arrow) and when the battery is removed the power supply is also interrupted, which otherwise directs the power to the active electronic circuits via a bipolar battery contact (BC). In order not to consume power when the hearing aid is not in use, there is also a mechanical switch (S) by means of which the patient may turn off the power, or the patient will have to remove the battery from the battery contacts.

One drawback with implantable hearing aids is that they have high electric power consumption as there are inevitable losses related to the inductive link during transmission of energy through the intact skin. As the carrier wave of the inductive link must remain full-on the whole time disregarding sound levels the useful lifetime of the battery may to appear short as compared to battery life time in a conventional hearing aid. The battery present in the external unit lasts 5-7 days for BCI and MEI (depending on how many hours a day the device is used) while for the CI and ABI the useful lifetime of the battery is even shorter as these also have implanted electrical circuits which have a substantial power consumption. It is therefore of utmost importance that the devices are turned off when they are not in use, e.g. at night, or temporarily when it is not necessary to listen via the implant not to consume battery capacity unnecessarily.

It is also important to stress that implantable hearing aids, which make use of a tuned inductive link for transmitting the signal and energy, consume considerably more power if they are not positioned above the implanted unit. This occurs as the tuned circuit for the carrier wave generated in the external unit is no longer tuned to the actual load impedance when it is removed from the head of the patient. Due to changes in the impedance conditions of the induction link the output stage will therefore require even more power than if it is attached to the head of the patient. It can be mentioned that the external unit may be split into two parts where only the transmitting coil (TC) and the external retention magnet (EM) are located in situ on top of the implanted unit (see the parallel dotted line which divides the external unit in two parts in FIG. 1). The remaining part of the external unit is advantageously located in a different housing worn on the pinnae of the outer ear (typically like a behind-the-ear device). This solution is typically used in CI and ABI as they have more than one battery and are therefore heavier than would be suitable to be carried by the retention magnets (would require stronger magnets which may give rise to circulation problems in the soft tissue which will be exposed to a higher pressure).

Implanted hearing aids often use a manual mechanical switch (S) to turn on/turn off the power consumption as shown in FIG. 1 (prior art). As manually activated switches require a relatively large amount of space and may be difficult to handle, some implantable hearing aids have instead made use of the fact that the battery can be removed or moved enough to cut off the power supply through the battery contacts (BC), see double headed arrow in FIG. 1. Both methods require an effort from the patient to turn on/off the power consumption. Compared to conventional air conduction hearing aids and bone anchored hearing aids the patient will not get an indication that the external device is turned off (conventional hearing aids will emit a squeaking sound if they are not turned off and not fitted to the patient). Many elderly have impaired dexterity and may have motoric difficulties to use a small manually activated power switch or to visually inspect whether a mechanical switch is turned "on" or "off".

One way to accomplish an automatic turning on/off of the power supply is to make use of the changes in the static magnetic flux density which occurs when the external unit is attached. In such a solution a magnetically actuated "reed relay" can be placed at a location so that the relay will be activated when the external unit is fixed in its position and is deactivated when the external unit is removed, see for example U.S. 2005/0033383. With "reed relay" is meant a relay that is activated by a static magnetic field that will exceed/fall below a certain level. When the external unit is fixed in its location the magnetic flux density will increase locally in certain areas and the "reed relay" is therefore advantageously placed in such an area so that the relay will detect this change in magnetic flux density and thereby turn on the power consumption. As an alternative to a reed relay the changes in the static magnetic flux density can be detected by using a Hall sensor. This sensor is thus sensing the static flux and produces a proportional electric voltage. A control circuit can then amplify this quite small electric voltage and at an appropriate selected voltage level from the Hall sensor, the control circuit can activate a relay that switches the power on and off, see for example U.S. 2011/0112607 A1 or U.S. 2005/0105752 A1. All these methods of controlling the power consumption has been considered to be relatively sensitive, especially as the external unit has a permanent magnet in place although the unit has been removed from the patient. This means that the relay only can make use of a change in the static magnetic flow at engagement of the external unit to the implanted unit in order to activate the power supply. Also, a solution using a Hall sensor requires additional electronic components to activate a relay that switches on/off the power from the battery. Such solutions may therefore be both bulky and costly.

Therefore, there is a need for a more inexpensive and reliable alternative device that automatically, directly or indirectly, activates the power supply in the outer unit when it is fitted to the patient and which inactivates or turns off/reduces the power consumption when the external unit is removed from the patient.

SUMMARY

A technique to automatically and reliably turn on/off the power consumption in an implantable hearing aid having magnets as its retention system is disclosed. The power consumption is turned on automatically when the hearing aid is fixed in place and is turned off automatically when the hearing aid is removed by the activation of a mechanical electric switching device by means of the static mechanical force which is developed between the retention magnets when the device is fitted in place.

According to an embodiment, an implantable hearing aid comprising an implanted unit located beneath skin for electrical, mechanical, or acoustic sound stimulation, and an external unit placed outside the skin is disclosed. The external unit is contained in a housing which is completely or partially surrounded by a shell. The external unit comprises a sound processor containing microphones for registration of sound, a signal processor for processing of sound information, a modulator for modulation and control of an output signal, and a battery for power supply, a transmitting coil for inductive transmission of the sound signal to the implanted unit, and one or more external magnets. The one or more external magnets creating a mutual static mechanical retention force with one or more retention magnets in the implanted unit which retains said housing in place on top of said implanted unit. The static mechanical retention force thus created affects an electric switching device such that said electric switching device directly or indirectly activates the power supply for the sound processor when said housing is installed on top of the implanted unit, and directly or indirectly turns off/reduces the power supply when said housing is removed.

In an embodiment, the electric switching device is a pressure or pull activated electric switching contact which is placed between the one or more external magnets and the shell of the housing such that a mechanical pressure or pulling force is created on top of said electric switching contact which is large enough to activate the electric switching device when said housing is installed on top of the implanted unit.

In an embodiment, the electric switching contact is placed between a skin-facing side of the one or more external retention magnets and the shell and is pressure activated as the one or more external retention magnets press the electric switching contact towards the shell of the housing when the external unit is installed on top of the implanted unit.

In an embodiment, the electric switching contact is fixed to a rear wall of the shell or other integrated internal wall of the housing, for example the printed circuit board, on a lateral side of the one or more external retention magnets, i.e. the side of the one or more external magnets furthest away from the skin, such that a pulling force is created as the one or more external retention magnets are brought in close contact with the one or more implanted retention magnets when the external unit is installed on top of the implanted unit.

In one embodiment, the implantable hearing aid may be a bone conductive implant (BCI) where the implanted unit comprises a receiving coil which inductively receives sound information from the sound processor and sound energy drives a bone conductive vibrator connected to a skull.

In a further embodiment, the implanted hearing aid may be a cochlear implant or a brainstem implant where the implanted unit comprises a receiving coil which inductively receives sound information from the sound processor, and where sound energy is converted to electrical impulses which stimulate an auditory nerve or brain stem or some other part of a brain.

In still a further embodiment, the implanted hearing aid may be a middle ear implant where the implanted unit comprises a receiving coil which inductively receives the sound information from the sound processor, and where sound energy is converted to mechanical vibrations which stimulate bones of a middle ear or liquid of an inner ear directly or indirectly.

BRIEF DESCRIPTION OF THE DRAWINGS

The embodiments of the disclosure, together with its advantages, may be best understood from the following detailed description taken in conjunction with the accompanying figures in which.

DETAILED DESCRIPTION

Figure 2:
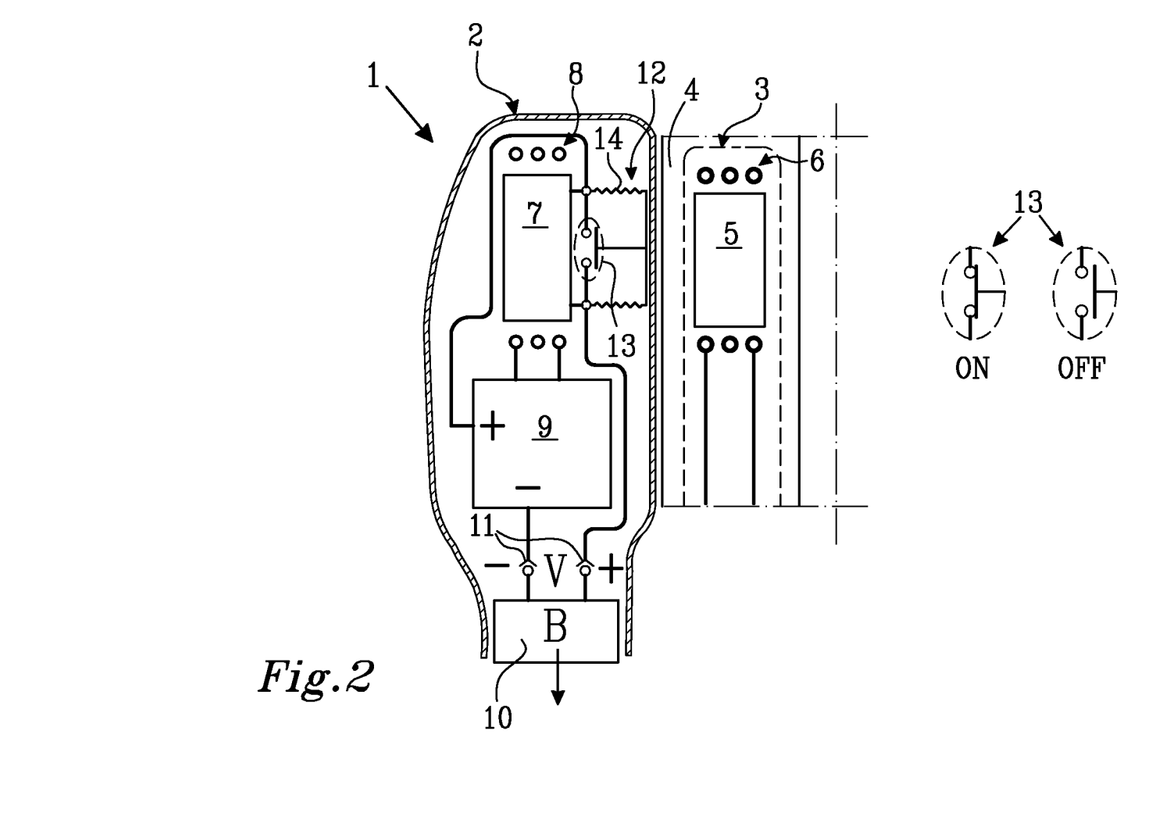
FIG. 2 shows the cross-section of one embodiment of the disclosure wherein the electric switching device is an electric switching contact activated by a pressing force which is formed between the retention magnets.

One application of the disclosure that achieves automatic activation/deactivation of the power consumption in implantable hearing aids is shown in FIG. 2. The external unit 1 of the implantable hearing aid is contained in a housing which is completely or partially surrounded by a shell 2. The external unit 1 is positioned on top of the implanted unit 3 which is located subcutaneously i.e. below intact skin and superficial soft tissue 4. For the sake of simplicity, the implanted unit 3 in FIG. 2 only shows the implanted retention magnet 5 (IM in FIG. 1) and the receiving implanted coil 6 (RC in FIG. 1) while the electronic unit (E) and the actuators (BCI, MEI, CI or ABI) are not shown. The external unit 1 contains an external retention magnet 7 and a transmitting coil 8 which when the external unit 1 is fitted to the patient, are centered directly next to the implanted retention magnet 5 and the receiving coil 6 of the implanted unit 3.

Furthermore, the external unit 1 contains an electronic unit 9 which contains the typical hearing aid components, which are also shown in FIG. 1 (Prior Art) such as microphones, a signal processor and driving electronics. One or more batteries 10 delivering a suitable voltage (V) are used as a power supply for the electrical unit 9. The batteries can easily be exchanged when they have been drained by removing them from the battery contacts 11 in the direction of the arrow (FIG. 2).

In order to safely turn on/off the power consumption in an implantable hearing aid, the external unit 1 of the hearing aid further comprises an electric switching device 12 which automatically activates the power supply when the hearing aid is fitted to a patient, and deactivates the power supply when it is removed from the patient. The electric switching device 12 is preferably an electric switching contact 13 using a conducting metal sheet as illustrated in FIGS. 2, 3, 4 and 5. The electric switching contact 13 is placed between the shell 2 of the external unit housing 1 and either side of the external retention magnet 7 such that the electric switching contact 13 can be activated by the pressure or pulling force which arises when the external retention magnet 7 and the implanted retention magnet 5 are brought close together.

In this respect the electric switching contact 13 is in an open condition if the external retention magnet 7 is not influenced by the mutual force developed from the implanted retention magnet 5, i.e. when the external unit 1 is not fitted to the patient. In order for the electric switching device 12 to achieve this function, the sheet metal of the electric switching contact 13 has a resilient suspension 14 which puts the electric switching contact 13 into an open state (OFF) when the external unit 1 is unused and puts the electric switching contact 13 into a closed state (ON) when the external unit 1 is located on top of the implanted unit 3 under influence of the mutual attraction force from the magnets (see enlarged part of FIG. 2).

In one embodiment the electric switching contact 13 is placed between the skin-facing side of the external retention magnet 7 and the shell 2 (see FIGS. 2 and 3a and b), such that a pressing force is created as the external retention magnet 7 presses the electric switching contact 13 towards the shell 2 of the housing when the external unit is fitted on top of the implanted unit.

Figure 3A:
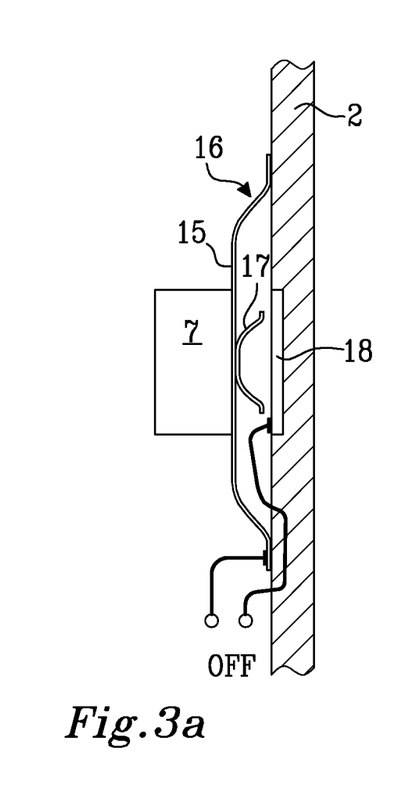
FIGS. 3a and 3b show the cross-section of one embodiment of the disclosure wherein the electric switching device comprises a pressure activated leaf spring.
Figure 3B:
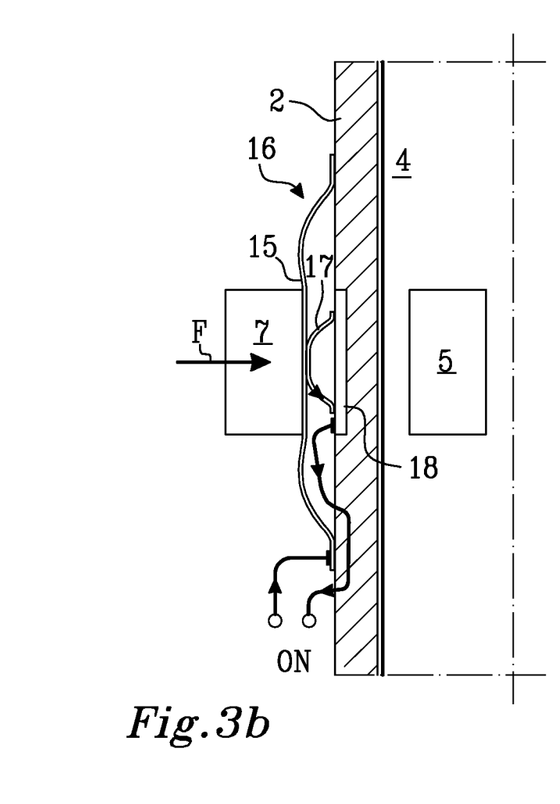
Figure 4A:
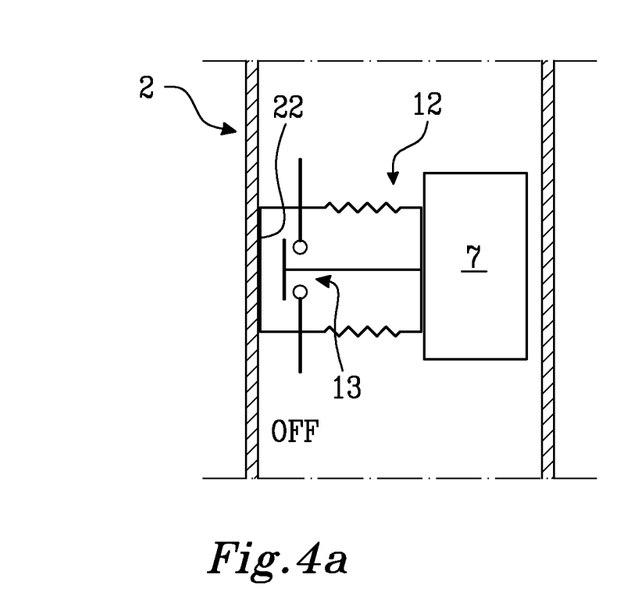
FIGS. 4a and 4b show the cross-section of one further embodiment of the disclosure wherein the electric switching device is activated by a pulling force.
Figure 4B:
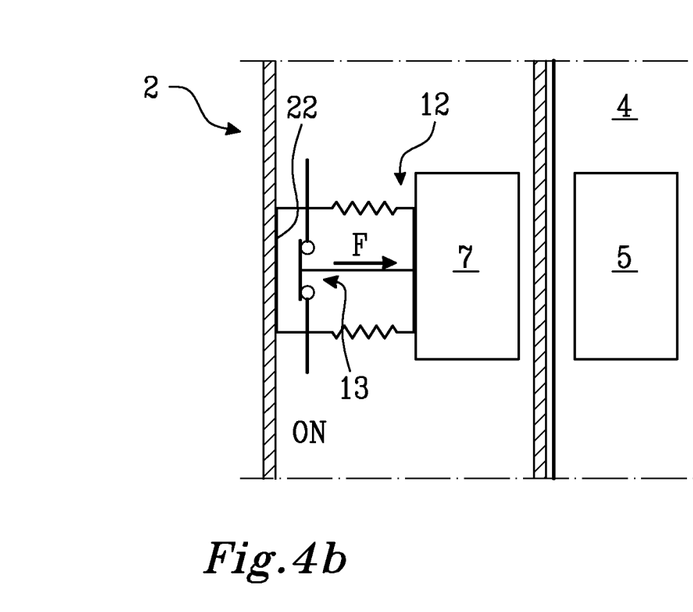

In order to obtain the minimum size for the electric switching device 12 in the axial direction in the chosen exemplary embodiment, the external retention magnet 7 has been mounted on a thin and electrically conductive leaf spring 15 with resilient arms 16 and where this electrically conductive leaf spring 15 also has a first sheet metal with points of contact 17 as shown in FIG. 3a. When the external retention magnet 7 is subjected to an attractive force F from the implanted retention magnet 5, an electrical contact is obtained between the points of contact 17 of the first conductive metal sheet and a second conductive metal receiving sheet 18 by which a conductive electric is formed through the electric switching device 12 as illustrated by the arrowheads in FIG. 3b. The condition when the electric switching device 12 closes the circuit (ON) is used to connect the battery 10 to the electrical unit 9 which then will be activated, see FIG. 2. When the external unit 1 is again removed from the implanted unit 3 the force F disappears and the electric switching device 12 breaks the circuit and the battery 10 is disconnected, i.e. the electrical unit 9 is deactivated (OFF).

The electric switching function of the electric switching device 12 can also be used to disable/enable a power down function in the sound processor itself. When the sound processor is "Disabled" the power consumption is reduced to a minimum which is often called "Power down". In this application the electric switching device 12 performs a logical function to activate/deactivate the power consumption. When e.g. the electric switching device 12 is in a closed state, a high voltage (typically about equal to the battery voltage) is generated on a terminal on the computer chip which results in an activation of the power consumption from the battery 10 and the corresponding breaking state generates a low voltage (typically around zero volts) which deactivates the power consumption or vice versa.

It can be noted that the bending of the electrically resilient leaf spring 15 has been exaggerated in FIG. 3 to illustrate the principle of the electric switching device 12, while in practice the electric switching device 12 has a thickness of the order of 0.5 mm which marginally affects the retention force. Furthermore it can be noted that the resilient arms 16 of the electrically resilient leaf spring 15 can be shaped in a way such that also a relatively small force (typically 0.1-0.6 N) can activate the electric switching device 12 which makes the electric switching device 12 less sensitive to variations in the retention forces of the magnets for different skin thicknesses.

In another embodiment (shown in FIG. 4) the electric switching contact 13 is fixed to the rear wall 22 of the shell or other wall integrated with the housing, for example the printed circuit board, on the lateral side of the external retention magnet 7, i.e. the side furthest away from the skin (see FIG. 4), such that a pulling force is created as the external retention magnet 7 is brought in close contact with the implanted retention magnet 5 when the external unit is fitted on top of the implanted unit. In this embodiment the sheet metal shield of the electric switching contact 13 is pulled by the external retention magnet 7 such that the electric switching device 12 closes.

Figure 5:
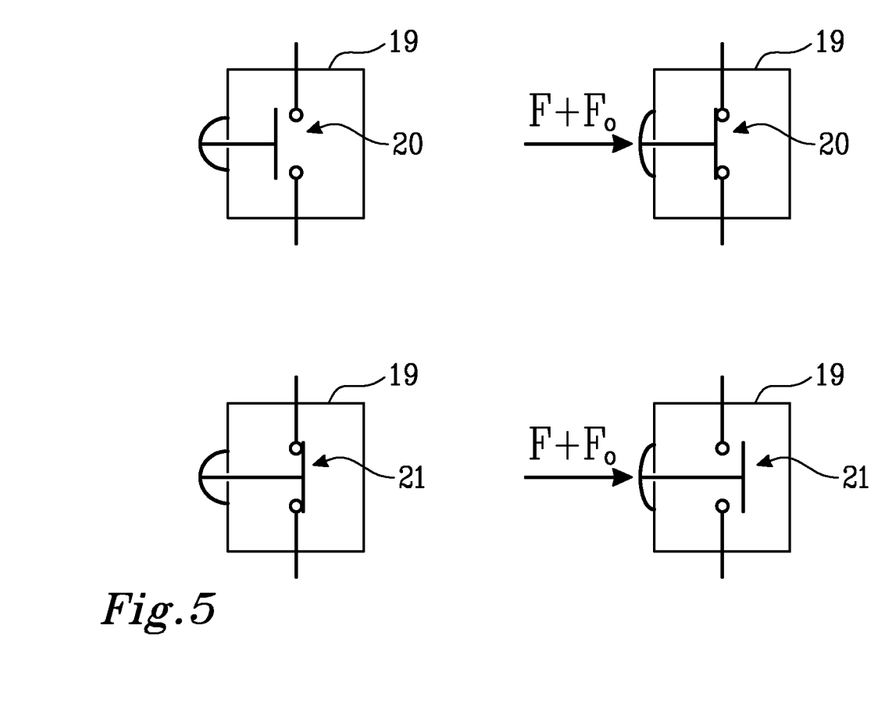
FIG. 5 shows the cross-section of one embodiment of the disclosure wherein the electric switching device comprises a micro-switch.

In a different embodiment a prefabricated so called micro-switch 19 can be used as electric switching device 12 (shown in FIG. 5). Such a switch is commercially available on the market and can be obtained in a normally open 20 alternatively a normally closed 21 state. The disadvantage with these available micro-switches is that they are fabricated for manual activation with an activation force of about 1 Newton which is of the same magnitude or higher than the retention force in implantable hearing aids. A use of such micro-switches in these applications requires that the micro-switch 19 is pre-pressed with a certain force F0 such that the retention force F added to F0 is able to activate the electric switching device 12. Generally these micro-switches are thicker than 0.5 mm which also requires a stronger retention magnet to compensate for a longer distance between the magnets which as mentioned above gives rise to certain medical disadvantages.

It can be seen from the illustrations in each one of the FIGS. 2, 3, 4, 5, or when combined that there is a number of different possibilities to implement the present invention. Notwithstanding that a limited number of different embodiments have been presented to illustrate the invention, it is evident that a person skilled in the art can alter, add or reduce details without deviating from the field of application and the basis of this invention which is defined by the appended claims.

REFERENCES

Håkansson B., Sabine Reinfeldt, Måns Eeg-Olofsson, Per Östli, Hamidreza Taghavi, Johannes Adler, John Gabrielsson, Stefan Stenfelt, Gösta Granström, 2009, A novel bone conduction implant (BCI)—engineering aspects and pre-clinical studies, International journal of audiology 2010; 49 (3):203-15.

LIST OF REFERENCE NUMERALS IN FIGURES

1 external unit (EU)
2 shell for the housing
3 implanted unit (IU)
4 intact skin
5 implanted retention magnet (IM)
6 implanted receiving coil (RC)
7 external retention magnet (EM)
8 transmitting coil (TM)
9 electrical unit
10 battery (B)
11 battery contacts (BC)
12 electric switching device
13 electric switching contact
14 resilient suspension
15 electrically conductive leaf spring
16 resilient arm
17 points of contact on a first sheet metal shield
18 second receiving sheet metal shield
19 micro-switch
20 normally open switch
21 normally closed switch
22 rear (lateral) side of the shell on the external unit

The invention claimed is:

1. An implantable hearing aid comprising:
an implanted unit configured to be located beneath skin for electrical, mechanical, or acoustic sound stimulation; and
an external unit configured to be placed outside the skin, said external unit is contained in a housing which is completely or partially surrounded by a shell, and comprises a sound processor containing microphones for registration of sound, a signal processor for processing of sound information, a modulator for modulation and control of an output signal, a battery for power supply, a transmitting coil for inductive transmission of the sound signal to the implanted unit and one or more external magnets, said one or more external magnets creating a mutual static mechanical retention force with one or more retention magnets in the implanted unit, and said mutual static and mechanical retention force retains said housing in place on top of said implanted unit, wherein said mutual static mechanical retention force thus created affects an electric switching device such that said electric switching device directly or indirectly activates power for the sound processor when said housing is installed on top of the implanted unit and directly or indirectly turns off/reduces the power supply when said housing is removed.

2. The implantable hearing aid according to claim 1, wherein the electric switching device is a pressure or pull activated electric switching contact which is placed between the one or more external magnets and the shell of the housing such that a mechanical pressure or pulling force is created on to said electric switching contact which is large enough to activate the electric switching device when said housing is installed on top of the implanted unit.

3. The implantable hearing aid according to claim 2, wherein the electric switching contact is placed between a skin-facing side of the one or more external retention magnets and the shell of the housing, and is pressure activated as the one or more external retention magnets press the electric switching contact towards the shell of the housing when the external unit is installed on top of the implanted unit.

4. The implantable hearing aid according to claim 2, wherein the electric switching contact is fixed to a rear wall of the shell or integrated with another wall within the housing on a lateral side of the one or more external retention magnets, such that a pulling force is created as the one or more external retention magnets is brought in close contact with the one or more implanted retention magnets when the external unit is installed on top of the implanted unit.

5. The implantable hearing aid according to claim 1, wherein the implantable hearing aid is a bone conductive implant where the implanted unit comprises a receiving coil which inductively receives the sound information from the sound processor and sound energy drives a bone conductive vibrator configured to be connected to a skull.

6. The implantable hearing aid according to claim 1, wherein the implanted hearing aid is a cochlear implant or a brainstem implant where the implanted unit comprises a receiving coil which inductively receives the sound information from the sound processor and where sound energy is converted to electrical impulses which are adapted to stimulate an auditory nerve or brain stem or some other part of a brain.

7. The implantable hearing aid according to claim 1, wherein the implanted hearing aid is a middle ear implant where the implanted unit comprises a receiving coil which inductively receives the sound information from the sound processor and where sound energy is converted to mechanical vibrations which are adapted to stimulate bones of a middle ear or liquid of an inner ear directly or indirectly.

* * * * *